United States Patent [19]
von Emster

[11] Patent Number: 5,248,308
[45] Date of Patent: Sep. 28, 1993

[54] OSTOMY POUCH COVER

[76] Inventor: Edward E. von Emster, 765 San Antonio Rd. #40, Palo Alto, Calif. 94303

[21] Appl. No.: 906,879

[22] Filed: Jun. 29, 1992

[51] Int. Cl.$^5$ ............................................. A61F 5/44
[52] U.S. Cl. ................................. 604/337; 604/332
[58] Field of Search .................... 604/332–345, 604/317

[56] References Cited

U.S. PATENT DOCUMENTS

| | | | |
|---|---|---|---|
| 2,583,721 | 1/1952 | Beede | 604/345 |
| 3,468,310 | 9/1969 | Kimbell | 604/345 |
| 4,085,752 | 4/1978 | Canale | 604/332 |
| 4,331,148 | 5/1982 | Steer et al. | |
| 4,403,991 | 9/1983 | Hill | 604/337 |
| 4,439,191 | 3/1984 | Hogan | |
| 4,465,486 | 8/1984 | Hill | 604/337 |
| 4,495,662 | 1/1985 | Miller | 604/332 |
| 4,519,797 | 5/1985 | Hall | |
| 4,596,560 | 6/1986 | Simpson | 604/337 |
| 4,705,512 | 11/1987 | Faucher | |
| 4,938,747 | 7/1990 | Wallace | 604/317 |
| 4,955,879 | 9/1990 | Mervine | 604/317 |
| 5,026,362 | 6/1991 | Willet | |
| 5,135,520 | 8/1992 | Beaupied | 604/345 |
| 5,142,702 | 9/1992 | Piloian | 604/345 |

OTHER PUBLICATIONS

Confort Cover Advertisement *Ostomy Quarterly* vol. 28, No. 4, Fall 91.
Surfit Pouch Cover Package/Photo.
Confortwear Sales Brochure and Photo.
Foxy ® Pouch Cover Photo.
Sir Edward "G" Pouch Cover Photo.

*Primary Examiner*—Randall L. Green
*Assistant Examiner*—Rob Clarke
*Attorney, Agent, or Firm*—James J. Leary

[57] ABSTRACT

An ostomy pouch cover which is adapted to fit over an ostomy appliance. The top opening of the cover has a cover flap which opens wide to allow the cover to be slipped on or off the ostomy appliance. There is an adjustable stoma opening with overlapping tabs that easily adjust and fasten around the flange of an ostomy appliance. A wide opening at the bottom of the pouch cover can be unfastened to allow drainage of the pouch contents. There is a fastener at the bottom of the cover and a mating fastener near the top so that when the cover and the ostomy appliance inside of it are folded upward the cover can be secured in the folded position, holding the appliance up and out of the way.

6 Claims, 3 Drawing Sheets

OSTOMY POUCH COVER

FIELD OF THE INVENTION

The present invention relates to a cover for concealing and protecting an ostomy bag or pouch.

BACKGROUND OF THE INVENTION

An ostomy is a surgical procedure which creates an artificial opening in the abdomen which is connected to the intestinal tract or the urinary tract for the discharge of bodily waste. Ostomies are sometimes necessary when the normal function of the intestinal tract or urinary tract has been disrupted by disease, injury, or other pathological condition. When the opening or stoma is connected to the large intestines or colon, the surgical procedure is known as a "colostomy." When the small intestine or ileum is connected to the stoma it is known as an "ileostomy." When the urinary tract is connected to the stoma it is called a "urostomy."

Ostomates, as people who have had ostomy surgery are called, generally wear a bag or pouch connected to the stoma to collect fecal matter or urine discharged from the body. Modern ostomy pouches are connected to the stoma by an adhesive skin barrier which attaches the pouch to the body and protects the skin around the stoma from being irritated by the discharge entering the pouch. Pouches are made in one-piece or two-piece construction. The one-piece pouch comes with the skin barrier attached. The two-piece consists of a skin barrier and a flange onto which a variety of pouches can snap. Thus the skin barrier can be worn for several days and the pouch can be removed for cleaning or changing. Many ostomy pouches are drainable. For ileostomy pouches the drain is usually a large opening at the bottom of the bag that folds up and is held closed with a clip. Urostomy pouches generally have a drain tube with a valve or plug for closing the tube. Colostomy pouches generally do not have drainable openings at their bottoms and are referred to as "closed end" pouches.

Many ostomates are self-conscious about wearing an ostomy bag because of the unnatural appearance of the appliance itself and because the contents may be visible through the clear or translucent bag. Others may be concerned about the possibility of leaks from the ostomy pouch or from around the skin barrier that would be embarrassing and could soil the clothes of the wearer. These people would be likely to wear a cover that would conceal and protect the ostomy pouch.

A number of ostomy pouch covers have been proposed and are commercially available. The following are representative of the patented ostomy pouch covers: U.S. Pat. No. 4,331,148 to Steer and Edwards for a Deodorizing Ostomy Bag Cover; U.S. Pat. No. 4,439,191 to Hogan for an Ostomy Bag Cover; U.S. Pat. No. 4,519,787 to Hall for a Medical Appliance Pouch with Cover; and U.S. Pat. No. 4,705,512 to Faucher for an Ostomy Pouch Cover. All of the known prior art suffers from one or more drawbacks which the present invention seeks to overcome.

SUMMARY OF THE INVENTION

The primary objective of the present invention is to provide a cover which effectively conceals the ostomy appliance and its contents, and which provides an added degree of protection from leakage of the contents. It is also an objective to provide an ostomy pouch cover than can be quickly and easily installed and yet is securely fastened to the ostomy appliance. Another objective is to provide an ostomy pouch cover with an opening that is adjustable for different sizes of stoma or flanges on the ostomy appliance. A further objective of the invention is to provide an ostomy pouch cover that allows emptying or drainage of the pouch contents without the need to remove the pouch cover.

An important objective which is unique to this invention is to provide a means for folding the cover and the ostomy pouch inside it upward and securing them in the folded position. This temporarily holds the ostomy appliance up and out of the way so it takes up half its usual space. This feature is especially important during intimate moments when the ostomy pouch hanging down may interfere with the enjoyment of sexual relations.

With these objectives in mind, the ostomy pouch cover of the present invention takes the form of a cloth pouch which is adapted to fit over an ostomy appliance. The top opening of the cover has a cover flap which opens wide to allow the cover to be slipped on or off the ostomy appliance. There is an adjustable circular opening with overlapping tabs that easily adjust and fasten around the flange of the appliance. A wide opening at the bottom of the pouch cover can be unfastened to allow drainage of the pouch contents. There is a fastener at the bottom of the cover and a mating fastener near the top so that when the cover and the ostomy appliance inside of it are folded upward the cover can be secured in the folded position, holding the appliance up and out of the way.

A number of advantages accrue from the use of the ostomy pouch cover. The cloth of the cover muffles any rustling noises caused by movement of the ostomy appliance. The fabric is also more comfortable against the skin than the polymer material of the ostomy pouches. The fabric reduces skin irritation from scratchy appliances or clips, and the fabric absorbs any body perspiration that develops under the appliance. Other objects and advantages of the present invention will become apparent from a consideration of the following description and the accompanying drawings.

DETAILED DESCRIPTION OF THE INVENTION

Figure 1:
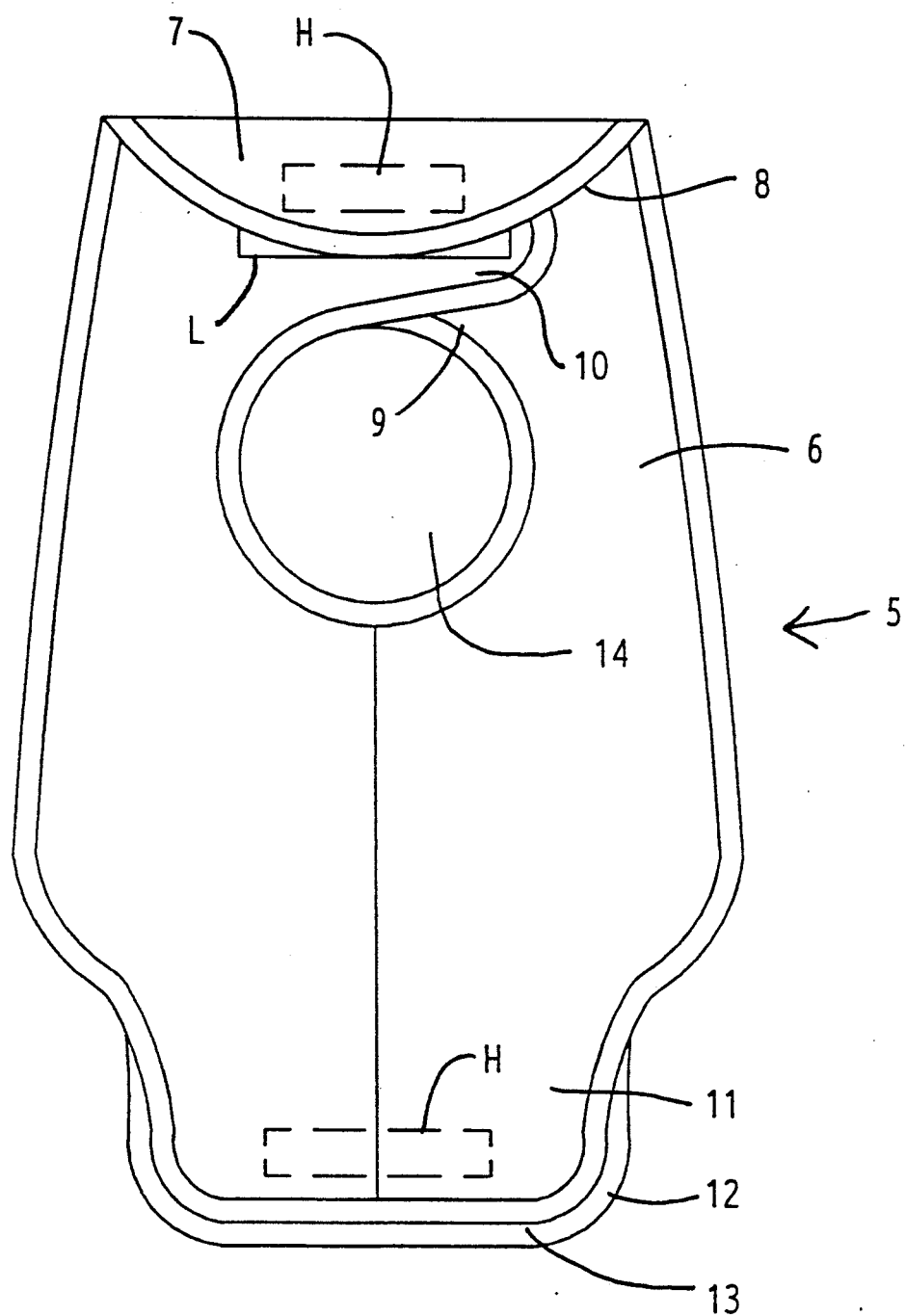
FIG. 1 shows a view of the ostomy pouch cover from the side facing the wearer.

The ostomy pouch cover 5 is preferably made form a woven or knitted fabric for comfort against the skin of the wearer. The ostomy pouch cover 5 is presently manufactured and sold in two fabrics, a 50%–50% cotton and polyester blend, and a 100% nylon tricot, though it could conceivably be made in almost any material which is knitted, woven, nonwoven, or could even be made of polymer sheet. The seams of the ostomy pouch cover 5 may be edged with bias tape, as shown in the drawings, for the further comfort of the wearer.

The ostomy pouch cover is shown in FIG. 1 as seen from the side that faces the wearer. The body of the cover 5 forms a pouch 6 that fits over the ostomy appliance. The cover 5 can be made in virtually any size to accommodate the variety of ostomy appliances in use. The top cover flap 7 closes the top opening 8 in the pouch 6. There is an adjustable opening 14, approximately circular in shape, that fits around the stoma and the flange on the skin barrier. This opening 14 is made adjustable in size by a pair of overlapping tabs 9, 10 that have mating hook H and loop L fasteners. By fastening the tabs 9, 10 together with more or less overlap the size of the opening 14 can be made smaller or larger.

This is a very advantageous feature of the present invention because the flanges or stoma openings of ostomy pouches can vary in diameter from 1.5 to 4 inches. With ostomy pouch covers of the prior art, the user was required to buy a cover with the exact size opening or to modify the cover by cutting a circular opening of the right size or to cut darts at the edge of the opening to widen it. Some of the prior art covers are even marked with concentric circles to aid the user in making the necessary modifications. None of this is necessary with the ostomy pouch cover of the present invention. The stoma opening 14 is automatically adjusted to the size of the flange by wrapping the tabs 9, 10 around the flange and fastening them together with the hook H and loop L fasteners. Thus, one size of opening 14 can adjust to fit a range of flange sizes. Presently, the ostomy pouch cover is made with two sizes of openings that cover the entire range of flange sizes: a small size that adjusts from 1.5 to 2.5 inches and a large size that adjusts from 2.5 to 4 inches. This greatly simplifies the selection and installation of ostomy pouch covers for the user.

The overlapping tabs 9, 10 also provide a secure attachment between the cover 5 and the flange of the ostomy pouch so that no other means of attachment is necessary. This is in marked contrast to many of the prior art ostomy pouch covers that relied on belts or special undergarments for attachment.

Figure 2:
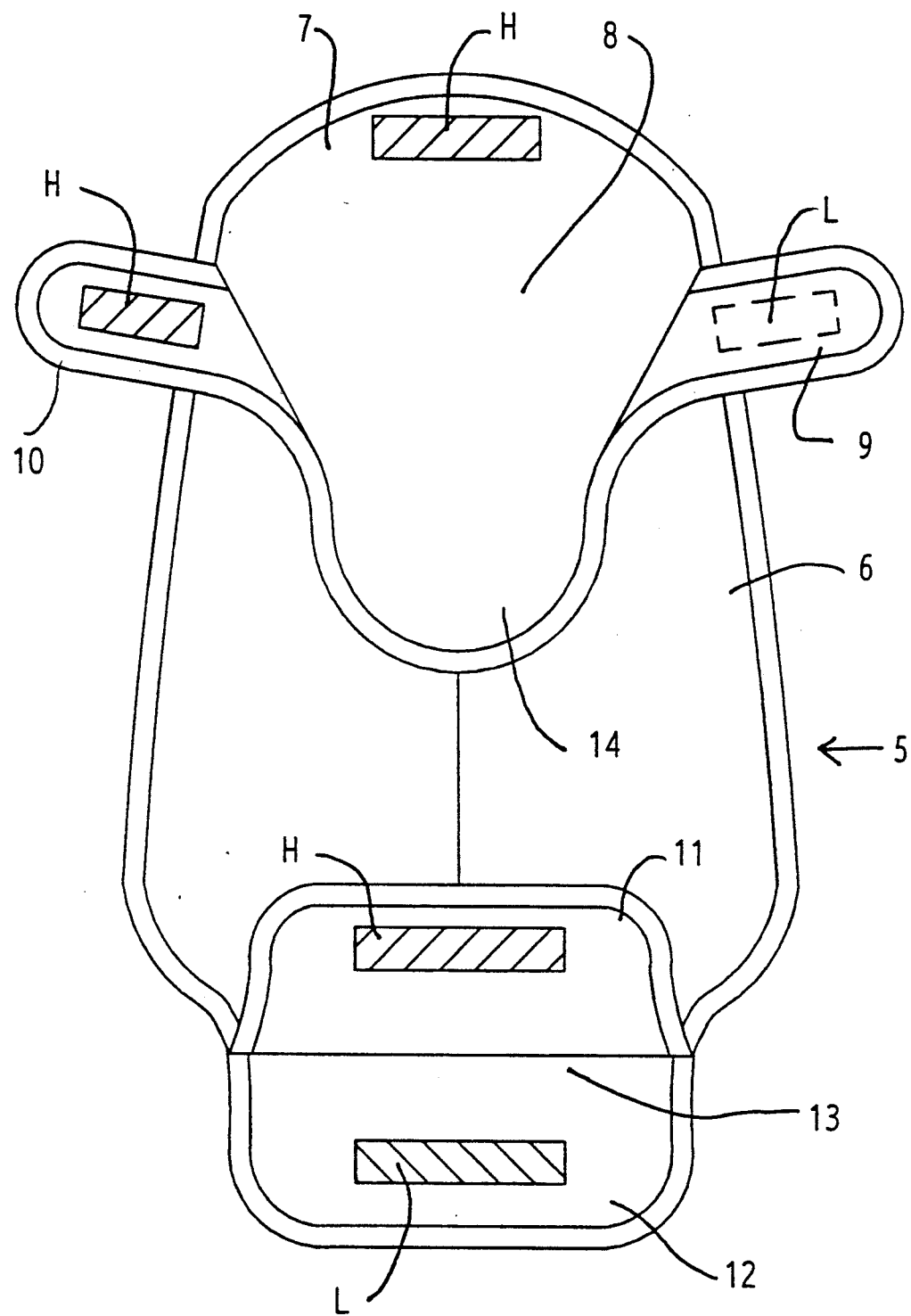
FIG. 2 shows the ostomy pouch cover opened up for installation over an ostomy pouch.

Another important advantage of the adjustable overlapping tabs 9, 10 on the stoma opening 14 can be clearly seen in FIG. 2. A severe disadvantage of most of the prior art ostomy pouch covers is that for installation the entire pouch had to be folded or wadded up and pushed through the small stoma opening in the cover. This was difficult and inconvenient, especially when the ostomy appliance was already attached to the user's abdomen. With the present invention, a wide top opening 8 is created by opening the top cover flap 7 and then unfastening the overlapping tabs 9, 10. This allows the user to easily slip the cover 5 on over the ostomy appliance, and then fasten it securely to the appliance by wrapping the stoma opening 14 around the flange and fastening the overlapping tabs 9, 10. The top cover flap 7 is then folded over the top opening 8 and fastened with mating hook H and loop L fasteners to conceal the appliance. The installation of the cover is quick, simple, and secure.

Another advantageous feature of the invention can be seen in FIG. 2. The ostomy pouch cover 5 has a bottom opening 13 to aid the user in draining the ostomy pouch. The bottom opening 13 is closed by a front flap 11 and a back flap 12 that fasten together with mating hook H and loop L fasteners. The bottom opening 13 allows the user access to the drain tube of a urostomy bag or the throat at the bottom of an ileostomy pouch, so that the pouch can be emptied without removing the cover 5. After the pouch has been drained the flaps 11, 12 are closed with the fasteners H, L so that the drain tube or clip on the pouch does not dangle below the cover 5. By contrast, many of the prior art ostomy pouch covers have no drainage opening so that the entire cover must be removed in order to empty the pouch. Other ostomy pouch covers that are made for drainable ostomy pouches have a bottom opening with no closure so that the drain tube or clip can dangle out of the opening which can be irritating and unsightly.

Figures 3, 4:
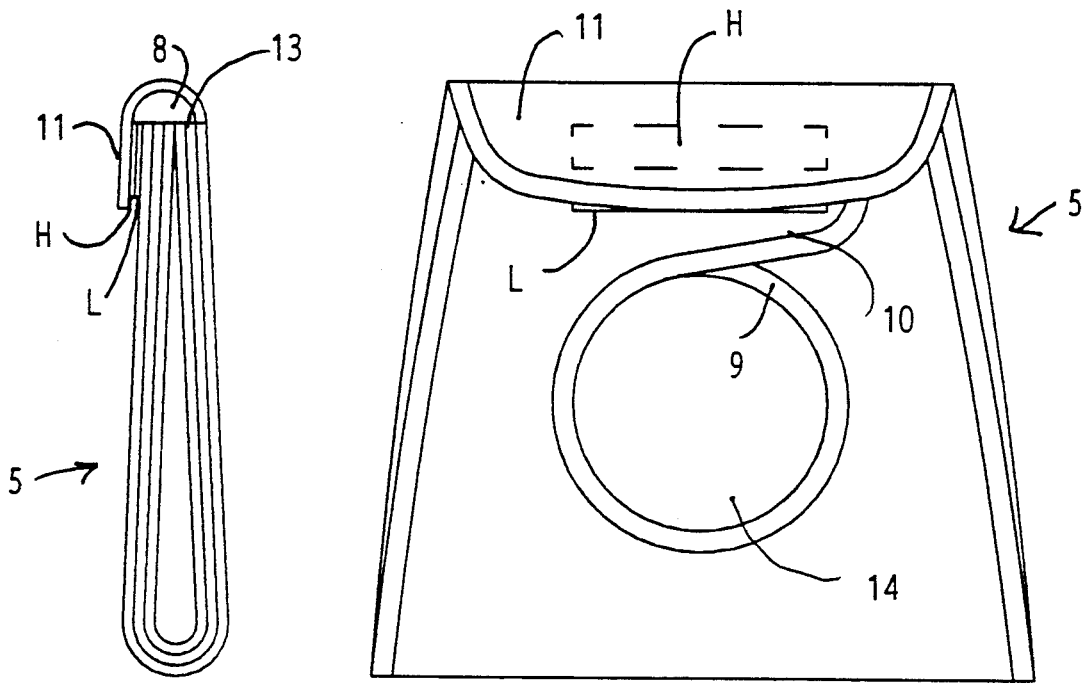
FIG. 3 shows the ostomy pouch cover in the folded position.
FIG. 4 shows a side view of the ostomy pouch cover in the folded position.

An extremely advantageous feature of the present invention is shown in FIGS. 3 and 4. The arrangement of the hook H and loop L fasteners on the ostomy pouch cover 5 allow the cover with the ostomy pouch inside to be folded upward and fastened in the folded position. FIG. 3 shows the ostomy pouch cover 5 in the folded position from the side facing the wearer. FIG. 4 shows a side view of the same ostomy pouch cover 5 in the folded position.

In order to place the ostomy pouch cover 5 in the folded position, the user first unfastens the top cover flap 7 and tucks it into the top opening 8. Then the user unfastens the bottom opening 13 and tucks the back flap 12 up inside. Then the bottom of the cover 5 is folded up and away from the wearer until it is even with the top of the cover 5. The front flap 11 is folded over the top opening 8 so that the hook fastener H attaches to the corresponding loop fastener L on the tab 10 just above the stoma opening 14.

In this position the cover 5 and the ostomy appliance inside only hang down half as far as usual. This moves the ostomy appliance up and out of the way so that it does not cause inconvenience, discomfort, or irritation that would interfere with the enjoyment of intimate moments.

CONCLUSION, RAMIFICATIONS, AND SCOPE

Thus it can be seen that the present invention provides an ostomy pouch cover with many features and advantages not exhibited by the prior art. It provides a cover which is quickly and easily installed over an ostomy appliance. It provides a secure attachment of the cover to the ostomy appliance, and the adjustable stoma opening allows adapting the cover to different sizes of flanges on the appliance. It allows drainage of the ostomy appliance without removing the cover, and it completely encloses the appliance when it is not being drained. Finally, it allows the cover, with the ostomy appliance inside, to be folded up and secured in the folded position.

Although the examples given include many specificities, they are intended as illustrative of only one possible embodiment of the invention. Other embodiments and modifications will, no doubt, occur to those skilled in the art. For instance, some or all of the fasteners, which have been described as hook and loop fasteners in the preferred embodiment, could be replaced with analogous fasteners such as snaps, buttons, magnets, or zippers without affecting the function of the invention. Thus, the examples given should only be interpreted as illustrations of some of the preferred embodiments of the invention, and the full scope of the invention should be determined by the appended claims and their legal equivalents.

I claim:

1. A cover for an ostomy appliance, comprising:

a pouch-like cover which substantially encloses said ostomy appliance, said cover having a top opening having a closure means, and said cover having a stoma opening, said stoma opening having a periphery which defines a continuous arc of greater than 360 degrees such that the ends of said arc overlap, the overlapping ends of said arc extending to form a first tab and a second tab, said first tab and said second tab having coacting fasteners attached thereto for removably fastening said first tab to said second tab, wherein said overlapping tabs separate said stoma opening from said top opening such that when said tabs are detached from one another, said stoma opening and said top opening are connected to one another to form a single opening.

2. The cover of claim 1 wherein said stoma opening has a diameter, and wherein said diameter of said stoma opening is adjustable by varying the extent to which said first tab and said second tab overlap one another.

3. The cover of claim 1 wherein said cover further comprises a bottom opening having a closure means, said bottom opening providing access to the bottom portion of said ostomy appliance.

4. The cover of claim 1 further comprising an attachment means proximate the top of said cover and a corresponding attachment means proximate the bottom of said cover, said cover having an extended position, and said cover having an alternate folded position in which the bottom of said cover is folded upward to meet the top of said cover, said cover being secured in said folded position by attaching said attachment means proximate the top of said cover to said corresponding attachment means proximate the bottom of said cover to hold said cover in said folded position.

5. A cover for an ostomy appliance, comprising:

a cover which substantially encloses said ostomy appliance, said cover having a top opening having a closure means, and said cover having a stoma opening which is adjustable in size, said stoma opening having a periphery which defines a continuous arc of greater than 360 degrees such that the ends of said arc overlap, the overlapping ends of said arc extending to form a first tab and a second tab, said first tab and said second tab having coacting fasteners attached thereto for removably fastening said first tab to said second tab whereby the size of said stoma opening is adjustable by varying the extent to which said tabs overlap one another, the overlapping tabs separating said stoma opening from said top opening such that when said tabs are detached from one another, said stoma opening and said top opening are connected to one another to form a single opening, and said cover having a bottom opening having a closure means, said bottom opening providing access to the bottom portion of said ostomy appliance.

6. The cover of claim 5 further comprising an attachment means proximate the top of said cover and a corresponding attachment means proximate the bottom of said cover, said cover having an extended position, and said cover having an alternate, folded position in which the bottom of said cover is folded upward to meet the top of said cover, said cover being secured in said folded position by attaching said attachment means proximate the top of said cover to said corresponding attachment means proximate the bottom of said cover to hold said cover in said folded position.

* * * * *